United States Patent [19]

Blum

[11] Patent Number: 4,894,467

[45] Date of Patent: Jan. 16, 1990

[54] VAPOR PHASE OXIDATION OR STYRENE TO STYRENE OXIDE

[75] Inventor: Patricia R. Blum, Macedonia, Ohio

[73] Assignee: The Standard Oil Company, Cleveland, Ohio

[21] Appl. No.: 919,722

[22] Filed: Oct. 16, 1986

[51] Int. Cl.$^4$ ............................................. C07B 301/10
[52] U.S. Cl. .................................. 549/534; 549/518; 549/523
[58] Field of Search ................................ 549/537, 534

[56] References Cited

U.S. PATENT DOCUMENTS

| | | | |
|---|---|---|---|
| 3,664,970 | 5/1972 | De Maio | 549/537 |
| 3,957,834 | 5/1976 | Piccinini et al. | 549/537 |
| 4,007,135 | 2/1977 | Hayden et al. | 549/537 |
| 4,061,659 | 12/1977 | Nielsen et al. | 549/534 |
| 4,212,772 | 7/1980 | Mross et al. | 549/537 |
| 4,248,740 | 2/1981 | Mitsuhata et al. | 549/537 |
| 4,248,741 | 2/1981 | Wernli et al. | 549/537 |
| 4,356,312 | 10/1982 | Nielsen et al. | 549/534 |

FOREIGN PATENT DOCUMENTS

| | | | |
|---|---|---|---|
| 486731 | 9/1952 | Canada | 549/537 |
| 494573 | 7/1953 | Canada | 549/537 |
| 2122913 | 1/1984 | United Kingdom | 549/534 |

OTHER PUBLICATIONS

English translation of Japanese Patent Publication No. 79-25,011, publication date: Aug. 24, 1979.
English translation of Y. Murakami et al, Nippon Kagaku Kaisha, No. 11, (1977), pp. 1603–1609.

*Primary Examiner*—Glennon H. Hollrah
*Assistant Examiner*—Susan P. Treanor
*Attorney, Agent, or Firm*—C. S. Lynch; D. J. Untener; L. W. Evans

[57] ABSTRACT

Disclosed is a process for making styrene oxide which comprises contacting styrene in the vapor phase with a molecular oxygen-containing gas over a silver metal catalyst containing a promoting amount of at least one alkali metal hydroxide selected from sodium, potassium and lithium hydroxides, on an inert solid inorganic support at contact times of from 0.6 to 10 seconds and temperatures from 200° to 350° C.

7 Claims, No Drawings

VAPOR PHASE OXIDATION OR STYRENE TO STYRENE OXIDE

This invention relates to an improved process for the vapor phase oxidation of styrene to styrene oxide over silver catalysts. The catalytic, vapor phase oxidation of ethylene to ethylene oxide, over silver based catalysts, is a well known and important industrial process. In contrast, a similar oxidation of styrene to styrene oxide has received only slight attention. See the work of Murakami et al. in Nippon Kagaku Kaishi, No. 11, pp 1603–9 (1977) and in Japanese patent publication 1979-25,011, publication date Aug. 24, 1979; and Zimmerman U.S. Pat. No. 2,992,238, issued July 11, 1961. In fact, the commercial route practiced for the production of styrene oxide utilizes a liquid phase reaction wherein the styrene is oxidized by an organic peroxycompound such as peracetic acid. The economics are expected to favor a vapor phase reaction using a heterogeneous catalyst and oxygen as the direct oxidant over the liquid phase reaction using a homogenous catalyst and the indirect peroxy oxidant, but until my invention no efficient vapor phase oxidation of styrene to styrene oxide existed.

It is an object of the invention to provide an improved process for the vapor phase oxidation of styrene to styrene oxide using a silver catalyst.

Other objects, as well as aspects, features and advantages, of the present invention will become apparent from a study of the accompanying disclosure and the claims.

The Murakami et al. references referred to above describe the use of a catalyst having silver on a support such as alumina, with various other oxides, particularly barium. However, the Murakami patent particularly cautions that, in the preparation of the catalyst, the alkali metal hydroxide must be thoroughly removed, stating that the contamination of the catalyst by even a very small quantity of an alkali metal may adversely affect the catalytic activity. In contrast to this teaching, I have found that a promoting quantity of certain alkali metal hydroxides in the supported silver catalyst is essential for obtaining improved results according to the present process.

On the other hand, Zimmerman in his cited patent discloses a method for making styrene oxide by oxidizing styrene using a supported silver catalyst which is prepared in a particular way and which can contain as a promoter, sodium hydroxide.

According to the present invention, there is provided a process for making styrene oxide which comprises contacting styrene in the vapor phase with a molecular oxygen-containing gas over a silver metal catalyst containing a promoting amount of at least one alkali metal hydroxide selected from sodium, potassium and lithium hydroxides, on an inert solid inorganic support at contact times of from 0.6 to 10 seconds and temperatures from 200° to 350° C.

In the present process usual temperatures are from 200° to 350° C., more usually 240° to 320° C.

The catalyst support in my process should have a surface area of less than 5 square meters per gram, usually less than 2 $m^2/g$.

The weight ratio of the alkali metal hydroxide to silver metal is usually at least 0.05, more usually at least 0.1. Although no upper limit is known, it is usual to use no higher ratio than 1.

The Zimmerman patent referenced above stressed a particular method of preparing a supported silver catalyst, but also indicated that various promoters could be added, icluding sodium hydroxide. Furthermore, the patent contains one example where "trace amounts" of sodium hydroxide were present in the catalyst. However, the patentee in column 2 specifies space velocities of between 500 and about 1100 volumes of gas per volume of catalyst per minute, stating that at space velocities lower than about 500, tendency is increasingly to oxidize the styrene further than to the oxide. A space velocity of 500 is the same as a contact time of 0.12 seconds, and a space velocity of 1100 is the same as a contact time of 0.0545 seconds. Thus, this reference teaches away from the present invention, which uses contact times at least five times as long as taught by the patentee and obtains clearly superior results at these high contact times, not the excessive burning taught by the patentee. It should be noted that the yield columns in the tables in the cited patent really record selectivities and not yields. Obviously, it is impossible to have yields of styrene oxide which are greater than the conversion of the styrene. Therefore, the tables obviously mean yield of styrene oxide based on styrene converted, which is in fact selectivity.

The preferred alkali metal hydroxide is NaOH. Also, barium hydroxide can be present in the catalyst, although it is not necessary. It does not appear to be a promoter but is a moderator that tends to minimize the burning to carbon oxides. Thus, in a catalyst containing silver promoted with the alkali metal hydroxide, if barium hydroxide is added, the tendency to form carbon oxides is lessened so that under a given set of conditions, less carbon oxides are formed using the barium hydroxide-containing catalyst that the catalyst in which the $Ba(OH)_2$ is absent.

Suitable inert supports having surface areas below 5 $m^2/g$ are silica, zirconia, titania, alumina, silicon carbide, zinc oxide, calcium hydroxide (and carbonate) and lanthanum oxide.

In this application, including the examples, the Na, K and Li compounds are expressed as the hydroxides, and it is believed that this is the alkali metal compound present. The barium in the initial catalyst (if present) is present as $Ba(OH)_2$, but during use in the conversion reaction, part of the barium is converted to $Ba(CO_3)_2$. However, the barium in this application is expressed as $Ba(OH)_2$.

Similarly, the calcium compound support is present as both $Ca(OH)_2$ and $CaCO_3$, with some CaO possibly being present depending on conditions. However, the calcium is expressed as $Ca(OH)_2$.

In the present oxidation process, the oxygen-containing gas can be oxygen or oxygen diluted with an inert diluent such as nitrogen (air is an example), heium or argon, for instance. For economic reasons, nitrogen is usually used.

The following examples of the invention are illustrative and are not to be considered as limiting. Comparative examples are also included.

In the following catalyst preparation examples 1–10, the compositions given for the catalysts are the values calculated from the batch materials, except for Example 4, which was analyzed; and Example 9, which is an analyzed composition, as further explained hereafter.

EXAMPLE 1

5.22 g of NaOH was dissolved in 50 ml of distilled $H_2O$, then the solution was impregnated onto 94.8 g of low surface area (1 $m^2/g$) alumina (8–30 mesh). The incipient wetness technique was used. After all of the NaOH solution had been added to the solid, the solid was dried in the oven at 115° C.

A solution of 5.83 g of $Ba(OH)_2.8H_2O$ dissolved in 40 cc of hot $H_2O$ of was inpregnated on 57 g of the alkali containing alumina. After all of the barium solution had been added the solid was dried in the oven at 115° C.

A solution containing 5.63 g of $(NH_4)_2CO_3$, 19.9 g of $AgNO_3$, 20 cc of conc. aqueous $NH_3$ and 20 ml of distilled water was impregnated on the Na and Ba containing support. After the last addition of the silver containing solution, the solid was dried at 115° C. overnight. Then the silver compound was reduced to Ag metal by treating with a flow of 66 cc/min of $H_2$ for 4 hours at 270° C.

The catalyst composition was 17.5 wt% Ag, 4.4 wt% $Ba(OH)_2$, 4.1 wt% NaOH and 74.1 wt% alumina support.

EXAMPLE 2

5.22 g of NaOH was dissolved in 50 ml of distilled $H_2O$, then the solution was impregnated onto 94.8 g of low surface area (1 $m^2/g$) alumina (8–30 mesh). The incipient wetness technique was used. After all of the NaOH solution had been added to the solid, the solid was dried in the oven at 115° C.

A solution containing 3.72 g of $(NH_4)_2CO_3$, 13.13 g of $AgNO_3$, 13 cc of conc. aqueous $NH_3$ and 13 ml of distilled water was impregnated on 40.2 g of the Na containing support. After the last addition of the silver containing solution, the solid was dried at 115° C. overnight. Then the silver compound was reduced to Ag metal by treating with a flow of 66 cc/min of $H_2$ for 4 hours at 270° C.

The catalyst composition was 17.2 wt% Ag, 4.3 wt% NaOH and 78.5 wt% alumina support.

EXAMPLE 3

4.43 g of KOH was dissolved in 25 ml of distilled $H_2O$, then the solution was impregnated onto 57 g of low surface area (1 $m^2/g$) alumina (8–30 mesh). The incipient wetness technique was used. After all of the KOH solution had been added to the solid, the solid was dried in the oven at 115° C.

A solution of 2.92 g of $Ba(OH)_2.8H_2O$ dissolved in 20 cc of hot $H_2O$ was impregnated on 30 g of the alkali containing alumina. After all of the barium solution had been added the solid was dried in the oven at 115° C.

A solution containing 2.82 g of $(NH_4)_2CO_3$, 9.95 g of $AgNO_3$, 10 cc of conc. aqueous $NH_3$ and 10 ml of distilled water was impregnated on the K and Ba containing support. After the last addition of the silver containing solution, the solid was dried at 115° C. overnight. Then the silver compound was reduced to Ag metal by treating with a flow of 66 cc/min of $H_2$ for 4 hours at 270° C.

The catalyst composition was 16.8 wt% Ag, 4.2 wt% $Ba(OH)_2$, 5.7 wt% KOH and 73.3 wt% alumina support.

EXAMPLE 4

Catalyst A of the Murakami article was made as described therein. Its composition was 20 weight percent silver, balance $Al_2O_3$.

EXAMPLE 5

13.13 g of CsOH was dissolved in 25 ml of distilled $H_2O$, then the solution was impregnated onto 57 g of low surface area (1 $m^2/g$) alumina (8–30 mesh). The incipient wetness technique was used. After all of the CsOH solution had been added to the solid, the solid was dried in the oven at 115° C.

A solution of 2.92 g of $Ba(OH)_2.8H_2O$ dissolved in 20 cc of hot $H_2O$ was impregnated on 30 g of the alkali containing alumina. After all of the barium solution had been added the solid was dried in the oven at 115° C.

A solution containing 2.82 g of $(NH_4)_2CO_3$, 9.95 g of $AgNO_3$, 10 cc of conc. aqueous $NH_3$ and 10 ml of distilled water was impregnated on the Cs and Ba containing support. After the last addition of the silver containing solution, the solid was dried at 115° C. overnight. Then the silver compound was reduced to Ag metal by treating with a flow of 66 cc/min of $H_2$ for 4 hours at 270° C.

The catalyst composition was 16.6 wt% Ag, 4.2 wt% $Ba(OH)_2$, 13.5 wt% CsOH and 65.7 wt% alumina support.

EXAMPLE 6

5.22 g of CsOH was dissolved in 25 ml of distilled $H_2O$, then the solution was impregnated onto 57 g of low surface area (1 $m^2/g$) alumina (8–30 mesh). The incipient wetness technique was used. After all of the CsOH solution had been added to the solid, the solid was dried in the oven at 115° C.

A solution of 2.92 g of $Ba(OH)_2.8H_2O$ dissolved in 20 cc of hot $H_2O$ was impregnated on 30 g of the alkali containing alumina. After all of the barium solution had been added the solid was dried in the oven at 115° C.

A solution containing 2.82 g of $(NH_4)_2CO_3$, 9.95 g of $AgNO_3$, 10 cc of conc. aqueous $NH_3$ and 10 ml of distilled water was impregnated on the Cs and Ba containing support. After the last addition of the silver containing solution, the solid was dried at 115° C. overnight. Then the silver compound was reduced to Ag metal by treating with a flow of 66 cc/min of $H_2$ for 4 hours at 270° C.

The catalyst composition was 16.6 wt% Ag, 4.2 wt% $Ba(OH)_2$, 6.7 wt% CsOH and 72.6 wt% alumina support.

EXAMPLE 7

1.83 g of LiOH was dissolved in 25 ml of distilled $H_2O$, then the solution was impregnated onto 55 g of low surface area (1 $m^2/g$) alumina (8–30 mesh). The incipient wetness technique was used. After all of the LiOH solution had been added to the solid, the solid was dried in the oven at 115° C.

A solution of 2.92 g of $Ba(OH)_2.8H_2O$ dissolved in 20 cc of hot $H_2O$ was impregnated on 28 g of the alkali containing alumina. After all of the barium solution had been added the solid was dried in the oven at 115° C.

A solution containing 2.82 g of $(NH_4)_2CO_3$, 9.95 g of $AgNO_3$, 10 cc of conc. aqueous $NH_3$ and 10 ml of distilled water was impregnated on the Li and Ba containing support. After the last addition of the silver containing solution, the solid was dried at 115° C. overnight.

Then the silver compound was reduced to Ag metal by treating with a flow of 66 cc/min of H₂ for 4 hours at 270° C.

The catalyst composition was 17.8 wt% Ag, 4.5 wt% Ba(OH)$_2$, 2.5 w% LiOH and 75.3 wt% alumina support.

EXAMPLE 8

A solution of 14.6 g of Ba(OH)$_2$.8H$_2$O dissolved in 75 cc of hot H$_2$O was impregnated onto 125 g of 8–30 mesh Al$_2$O$_3$ having 1 m$^2$/g surface area. The incipient wetness technique was used. After all of the barium solution had been added the solid was dried in the oven at 115° C.

A solution containing 14.1 g of (NH$_4$)$_2$CO$_3$, 49.8 g of AgNO$_3$, 50 cc of conc. aqueous NH$_3$ and 50 ml of distilled water was impregnated on the Ba containing support. After the last addition of the silver containing solution, the solid was dried at 115° C. overnight. Then the silver compound was reduced to Ag metal by treating with a flow of 66 cc/min of H$_2$ for 4 hours at 270° C.

The catalyst composition was 19.2 wt% Ag, 4.8 wt% Ba(OH)$_2$, and 76.0 wt% alumina support.

EXAMPLE 9

A catalyst of the invention using a calcium compound as support, and a small amount of CaO, was made as follows:

Preparation of the Support

Calcium nitrate (0.963 moles of Ca(NO$_3$)$_2$.4H$_2$O; 227 g) was dissolved in 500 ml of distilled water. Sodium hydroxide (3.92 moles of NaOH, 156.6 g) was dissolved in a second 500 ml portion of distilled water. The NaOH solution was added to the Ca(NO$_3$)$_2$.4H$_2$O solution and a calcium hydroxide-containing precipitate formed.

This white solid was collected on a filter and washed with 500 ml of distilled water. This white solid was dried at 110° then calcined for 2 hrs at 400° C. The final white solid was a mixture of calcium hydroxide, calcium oxide, calcium carbonate and 5.2% sodium hydroxide.

Preparation of the Catalyst

A solution of 5.83 g of Ba(OH)$_2$.8H$_2$O dissolved in 40 cc of hot H$_2$O was impregnated on 27.7 g of the above support. The incipient wetness technique was used. After all of the barium solution had been added the solid was dried in the oven at 115° C.

A solution containing 5.63 g of (NH$_4$)$_2$CO$_3$, 19.9 g of AgNO$_3$, 20 cc of conc. aqueous NH$_3$ and 20 ml of distilled water was impregnated on the Na and Ba containing support. After the last addition of the silver containing solution, the solid was dried at 115° C. overnight. Then the siver compound was reduced to Ag metal by treating with a flow of 66 cc/min of H$_2$ for 4 hours at 270° C.

The catalyst composition was 22 wt% Ag, 6.1 wt% Ba(OH)$_2$, 1,7 wt% NaOH and 30 wt% of Ca, present as some mixture of the oxide, hydroxide and carbonate. These values are from actual analyses, and the calcium compounds were identified by X-ray powder diffraction. The support calcium compounds as a whole comprise 70.2 weight percent of the catalyst composition.

EXAMPLE 10

To make the support for this catalyst, CaCO$_3$ was calcined at 800° C. The product was about 18 wt% CaCO$_3$, 1–2 wt% Ca(OH)$_2$, and 80 wt% CaO, as shown by X-ray powder diffraction analysis.

A solution of 5.83 g of Ba(OH)$_2$.8H$_2$O dissolved in 40 cc of hot H$_2$O was impregnated on 50 cc (25.3 g) of the above support, using the incipient wetness technique. After all of the barium solution had been added the solid was dried in the oven at 115° C.

A solution containing 5.63 g of (NH$_4$)$_2$CO$_3$, 19.9 g of AgNO$_3$, 20 cc of conc. aqueous NH$_3$ and 20 ml of distilled water was impregnated on the Ba containing support. After the last addition of the silver containing solution, the solid was dried at 115° C. overnight. Then the silver compound was reduced to Ag metal by treating with a flow of 66 cc/min of H$_2$ for 4 hours at 270° C.

The catalyst composition was 29 wt% Ag, 7.3 wt% Ba(OH)$_2$, and 52.3 wt% of the foregoing support.

The styrene oxidation examples were carried out by passing the feed gases over 20 cc of catalyst in a fixed bed reactor in a suitcase furnace. The temperatures in the furnace and in the reactor bed were measured. Table 1 summarized the conditions and results.

TABLE 1

| Example No. | Catalyst of Example No. | Molar Ratio Feed O$_2$/N$_2$/Styrene | Contact Time Seconds | Furnace /Bed Temp °C. | Styrene Conversion Percent | Styrene Oxide Yield Percent | Styrene Oxide Selectivity Percent |
|---|---|---|---|---|---|---|---|
| 11 | 1 | 10.2/3.1/1 | 2.46 | 279/285 | 20.56 | 17.33 | 84.32 |
| 12 | 1 | 10.2/3.1/1 | 2.49 | 282/292 | 23.78 | 19.68 | 82.74 |
| 13 | 2 | 4.2/15.4/1 | 2.21 | 271/280 | 24.59 | 19.52 | 79.39 |
| 14 | 3 | 10.2/3.1/1 | 2.97 | 279/284 | 13.19 | 11.21 | 85.00 |
| *15 | 4 | 4.7/17.1/1 | 2.32 | 262/260 | 2.93 | 0.33 | 11.24 |
| *16 | 5 | 10.2/3.1/1 | 3.02 | 274/273 | 0.77 | 0.49 | 63.64 |
| *17 | 6 | 4.2/15.4/1 | 2.36 | 278/281 | 1.12 | 0.86 | 77.37 |
| 18 | 7 | 4.2/15.4/1 | 2.39 | 271/275 | 10.79 | 9.10 | 84.31 |
| 19 | 7 | 10.2/3.1/1 | 2.95 | 279/286 | 16.01 | 12.01 | 75.00 |
| *20 | 8 | 4.3/10.7/1 | 2.20 | 273/279 | 7.85 | 2.21 | 31.22 |
| *21 | 8 | 10.5/3.2/1 | 2.68 | 278/290 | 11.97 | 3.75 | 32.84 |
| 22 | 9 | 10.5/3.2/1 | 2.66 | 280/296 | 30.78 | 18.30 | 59.47 |
| *23 | 10 | 4.2/15.4/1 | 2.51 | 271/275 | 2.77 | 0.68 | 24.73 |

*Comparative examples

A study of the table shows that the results obtained with the comparative examples, none of which contained potassium, lithium or sodium hydroxides, gave much lower yields of styrene oxide than the examples of the invention; moreover, the good yields of styrene oxide in the invention examples were obtained at high selectivities.

As will be evident to those skilled in the art various modifications of this invention can be made or followed in the light of the foregoing disclosure and discussion without departing from the spirit and scope of the disclosure or from the scope of the claims.

What is claimed is:

1. A process for making styrene oxide which comprises contacting styrene in the vapor phase with a molecular oxygen-containing gas over a silver metal catalyst containing a promoting amount of at least one alkali metal hydroxide selected from sodium, potassium and lithium hydroxides, on an inert solid inorganic support at contact times of from 0.6 to 10 seconds and temperatures from 200° to 350° C.

2. A process of claim 1 wherein the support has a surface area less than 5 m²/g.

3. A process of claim 1 wherein the temperature is from 240° to 320° C.

4. A process of claim 3 wherein the support has a surface area less than 5 m²/g.

5. A process of claim 1 wherein the alkali metal hydroxide includes a promoting amount of NaOH.

6. A process according to claim 1 wherein said promoting amount is such that the weight ratio of said alkali metal hydroxide(s) to silver metal is at least 0.05.

7. A process according to claim 5 wherein said promoting amount is such that the weight ratio of said alkali metal hydroxide(s) to silver metal is at least 0.05.

* * * * *

UNITED STATES PATENT AND TRADEMARK OFFICE
CERTIFICATE OF CORRECTION

PATENT NO. : 4,894,467

DATED : January 16, 1990

INVENTOR(S) : P. R. Blum

It is certified that error appears in the above-identified patent and that said Letters Patent is hereby corrected as shown below:

On the title page:

In the title delete "or" from the title and insert --of--.

In column 1, correct the title by deleting "or" and inserting --of--.

In column 3, paragraph 2, line 2, delete the word "inpregnated" and insert --impregnated--.

Signed and Sealed this

Twelfth Day of March, 1991

Attest:

HARRY F. MANBECK, JR.

*Attesting Officer*    Commissioner of Patents and Trademarks